(12) United States Patent
Stirzel

(10) Patent No.: US 8,413,652 B2
(45) Date of Patent: Apr. 9, 2013

(54) EVAPORATION ELEMENT FOR LIQUIDS

(76) Inventor: Alexander Stirzel, Ulm (DE)

( * ) Notice: Subject to any disclaimer, the term of this patent is extended or adjusted under 35 U.S.C. 154(b) by 0 days.

(21) Appl. No.: 12/376,711

(22) PCT Filed: Aug. 8, 2007

(86) PCT No.: PCT/DE2007/001411
§ 371 (c)(1),
(2), (4) Date: Jun. 30, 2009

(87) PCT Pub. No.: WO2008/017298
PCT Pub. Date: Feb. 14, 2008

(65) Prior Publication Data
US 2009/0301471 A1 Dec. 10, 2009

(30) Foreign Application Priority Data
Aug. 8, 2006 (DE) .......... 10 2006 037 031

(51) Int. Cl.
*A61M 15/00* (2006.01)
*A61M 15/06* (2006.01)
*A61M 16/00* (2006.01)
*F23D 11/00* (2006.01)
*F23D 14/00* (2006.01)

(52) U.S. Cl. .......... 128/203.26; 128/202.21; 128/203.21

(58) Field of Classification Search .......... 128/202.21, 128/203.12, 203.21, 203.26, 204.13, 205.22
See application file for complete search history.

(56) References Cited

U.S. PATENT DOCUMENTS

| | | |
|---|---|---|
| 2001/0042546 A1 | 11/2001 | Umeda et al. |
| 2005/0236006 A1 | 10/2005 | Cowan |
| 2006/0137535 A1 * | 6/2006 | Searle .......... 99/348 |

FOREIGN PATENT DOCUMENTS

| | | | |
|---|---|---|---|
| FR | 2065782 | | 8/1971 |
| FR | 2818152 | | 6/2002 |
| GB | 644025 | | 10/1950 |
| GB | EP0129985 | * | 5/1984 |
| GB | 2001002295 | * | 6/2001 |
| WO | 2005020726 | | 3/2005 |

OTHER PUBLICATIONS

Machine translation of FR2065782 (Bruwer), EPO, Jul. 26, 2012, 4 pages total.*

* cited by examiner

*Primary Examiner* — Oren Ginsberg
(74) *Attorney, Agent, or Firm* — Stolowitz Ford Cowger LLP

(57) ABSTRACT

An evaporation element for liquids, in particular aqueous solutions, has a first reservoir for storing the liquid that is to be evaporated, a second reservoir, which is separated from the first reservoir by a sheet and contains a reagent that in contact with the liquid that is to be evaporated carries out an exothermic chemical reaction, and an opening element which, on actuation, perforates the sheet and in this way brings the reagent into contact with the liquid that is to be evaporated.

7 Claims, 1 Drawing Sheet

EVAPORATION ELEMENT FOR LIQUIDS

This application is national phase filing of International Application No. PCT/DE2007/001411, filed on Aug. 8, 2007 and claims priority to German Application No. 10 2006 037 031.7, filed on Aug. 8, 2006, which are incorporated herein in their entirety by reference.

FIELD OF THE INVENTION

The invention relates to a vaporization element for liquids, in particular aqueous solutions, which can contain aromas and, for example, caffeine, nicotine and others, preferably for inhalation of the vaporized liquid.

RELATED PRIOR ART

Devices for heating liquids which contain aroma substances, such as, for example, essential oils or the like, for the purpose of inhalation of the liquid vapour impregnated with the aroma substances have been known for a long time.

Medical uses of inhalation of vaporizing liquids lie, for example, in the inhalation of essential oils for alleviating cold symptoms and diseases of the respiratory tract. A further use lies in the administration of nicotine, such as is described in the patent DE 10 2004 033 579 B4. In this context, a mixture of water, nicotine and aroma substances is vaporized, the aroma substances already vaporizing at relatively low temperatures of between 50 and 90° C. Nicotine itself vaporizes only at approx. 300° C., but is hygroscopic and can undergo steam distillation. There is therefore the possibility of already vaporizing a homogeneous nicotine-water mixture at relatively low temperatures. By uptake of the nicotine/aroma/steam mixture without simultaneous uptake of carcinogenic substances (chiefly condensate), as with nicotine uptake through smoke, this form of nicotine uptake opens up the possibility for nicotine enjoyment by uptake of a well-dosed amount of nicotine without at the same time having to take up carcinogenic substances, and without adversely affecting surrounding people or the like.

It is known from DE 10 2004 033 579 B4 to impregnate finely porous ceramic material with the vaporizing solution and to release the vapour again for inhalation by heating the ceramic element. In this context, an electrical heat source or an external heat source, such as a cigarette lighter or the like, can be employed as the heat source for the heating. However, a high energy demand, which can be satisfied only by a comparatively heavy and voluminous battery, is required for an electrical heat source. For a portable inhaling apparatus in particular, however, such a battery is impractical, too heavy and too expensive.

External heat sources, such as cigarette lighters or the like, can damage and soot up the inhaling apparatus because of the very high flame temperature and are therefore also not very user-friendly. Furthermore, handling a naked flame is associated with risks in many respects, and is undesirable because of the combustion products formed.

EP 0 371 282 A discloses an aerosol vaporization device comprising a heat source which is not based on a combustion operation, for example containing calcium oxide, which generates heat on contact with water, and a reservoir, which is separated from the heat source but in thermal contact with this, for the aerosol to be heated.

SUMMARY OF THE INVENTION

The present invention is therefore based on the object of providing a vaporization element for liquids which is compact and inexpensive and has diverse uses, in particular for inhalation purposes.

To achieve the object, a vaporization element for liquids, in particular aqueous solutions, is proposed, comprising a first reservoir for storage of the liquid to be vaporized, a second reservoir which is separated from the first reservoir by a film and has a reagent which carries out an exothermic chemical reaction in contact with the liquid to be vaporized, and an opening element which, when actuated, perforates the film and in this way brings the reagent into contact with the liquid to be vaporized.

In the vaporization element according to the invention, the liquid to be vaporized is heated by bringing the liquid itself into contact with the reagent, for example calcium oxide. By actuating the opening element, the film which separates the liquid to be vaporized from the reagent is perforated, so that the liquid reacts with the reagent and heat is released, which causes the liquid to vaporize. Compared with the aerosol vaporization device known from EP 0 371 282 A, the advantage achieved by the invention lies in particular in the simpler, less expensive and more space-saving construction. With the vaporization element present according to the invention, the most space-saving and favourable possibility of providing energy in a portable manner in a small space is utilized, and storage and release by a chemical route.

The vaporization element according to the invention preferably has a heat-resistant and waterproof housing, for example of plastic, e.g. polysulfone or polycarbonate or the like, and a cover part mounted on the housing such that it pivots over a hinge.

The opening element is formed, for example, by mandrels or pins arranged on the underside of the cover part mounted on the housing such that it pivots. However, alternative opening mechanisms, for example based on a rotating ring mounted like a diving watch, are likewise possible in the context of the invention, as is, for example, a mandrel arranged laterally in the housing or on the vaporization element itself.

The second reservoir can contain calcium oxide as the reagent. Contact with the aqueous solution to be vaporized leads to an exothermic chemical reaction.

The liquid to be vaporized can be an aqueous solution containing caffeine, nicotine and/or other aroma substances.

The vaporization element is preferably embedded in a heat-resistant and waterproof housing made of, for example, metal, clay or, preferably, plastic or the like. The housing can have an opening for inhalation of the vaporizing liquid, e.g. in the form of a folding snorkel.

The vaporization element with the housing can be so small and manageable in construction that a portable inhalation apparatus which can also be worn e.g. as bracelet, like a watch, results.

BRIEF DESCRIPTION OF THE DRAWINGS

The invention is described in the following with the aid of a preferred embodiment example with reference to the attached drawings.

DETAILED DESCRIPTION OF THE INVENTION

Figure 1:
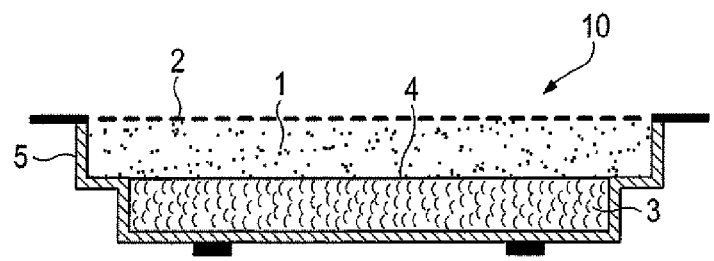
FIG. 1 shows an embodiment example of the vaporization element according to the invention without the housing, in cross-section.

FIG. 1 shows, in cross-section, an embodiment example of the vaporization element according to the invention without the housing, which is designated overall by the reference number 10. The vaporization element comprises a first upper reservoir 1 which serves as a liquid store for the aqueous solution to be vaporized. The aqueous solution in this context can contain caffeine, nicotine and/or other aroma substances.

The first reservoir 1 is separated by a thin film of plastic 4 from a second reservoir 3 which contains a reagent, such as, for example, calcium oxide. The first reservoir 1 and the second reservoir 3 are accommodated in a preferably waterproof and heat-resistant trough 5 or a bag, preferably of a heat-resistant film of plastic.

When the liquid to be vaporized contained in the first reservoir 1 comes into contact with the reagent in the second reservoir 3, the resulting chemical reaction generates sufficient heat to vaporize or to evaporate the liquid with the aroma substances contained therein. In order to trigger this reaction, the protective film 4 must be perforated, for which mandrels or pins 13 arranged on the inside of the pivoting lid 14 of the housing in the embodiment example shown in FIGS. 2 and 3 can serve. However, other mechanisms for perforation of the film 4 are of course likewise possible in the context of the invention.

Figure 2:
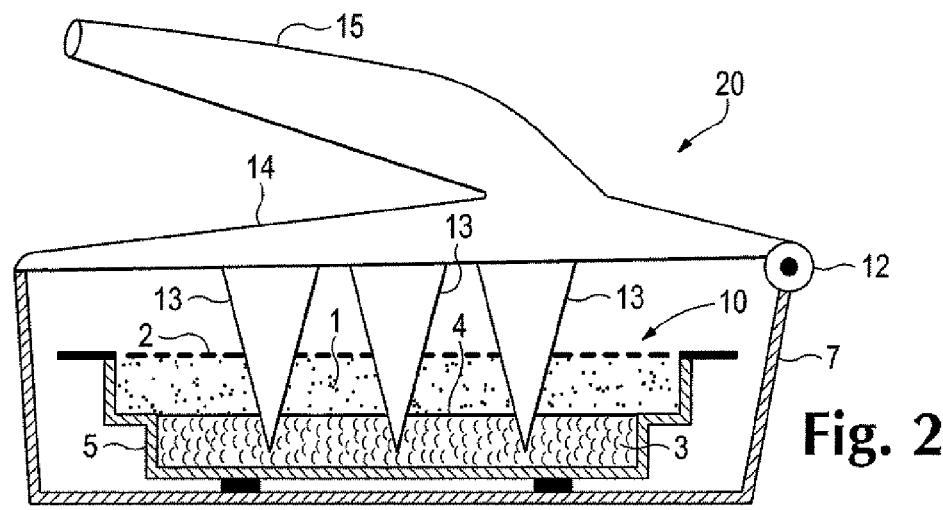
FIG. 2 shows the vaporization element with the housing and closed cover, in cross-section.
Figure 3:
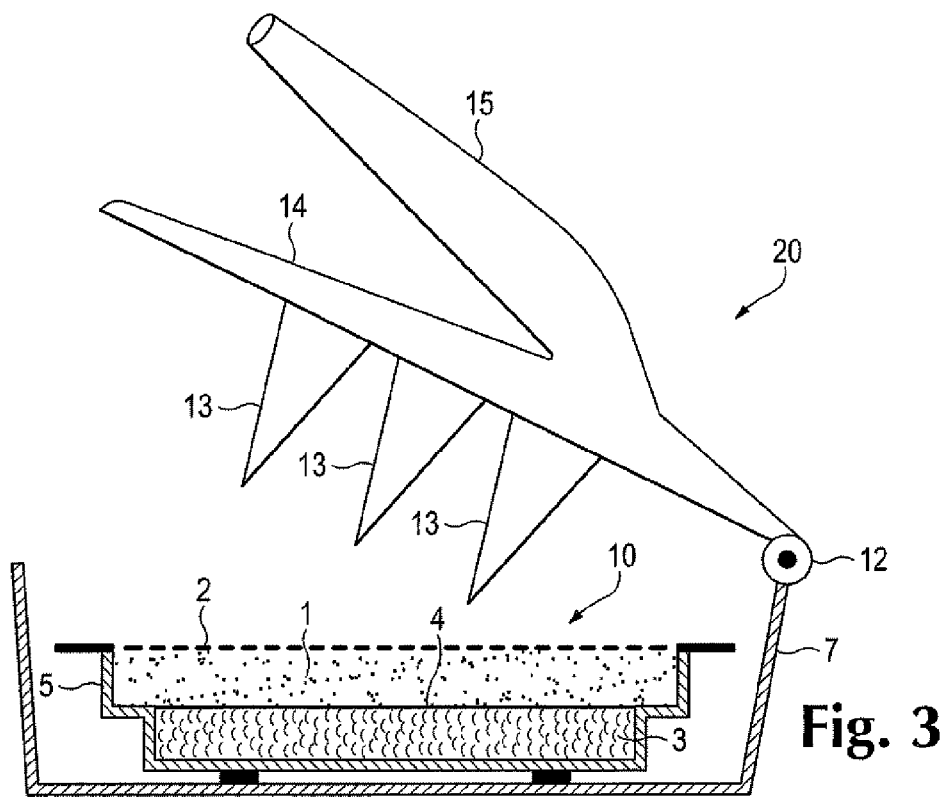
FIG. 3 shows the vaporization element with the housing and opened cover, in cross-section.

FIGS. 2 and 3 show in cross-section the vaporization element, designated overall by 20, with the housing and cover 14 mounted such that it pivots by means of the hinge 12, the cover 14 being open in the view shown in FIG. 2 and closed in the view shown in FIG. 3.

The user starts the vaporization operation by closing the cover 14, as a result of which the film 4 is perforated by the mandrels 13 and the chemical reaction is started. The vaporizing liquid containing the aroma substances escapes out via a second film 2 preferably comprising a film of plastic provided with openings. Alternatively, however, this second film 2 can also be omitted. The ascending vapour then passes through the opening 15 in the cover 14 to the outside.

For thermal insulation on the outside, the vaporization element according to the invention preferably has a thermally insulating housing 7 of plastic, ceramic or another suitable material. The embodiment example shown in FIGS. 2 and 3 shows a housing 7 with a cover 14 which has an opening 15, suitable for inhalation, which can be provided with a hose or the like. However, differently shaped housing forms are likewise possible. Hardly any limits are imposed on the freedom of design here. Instead of being rectangular or square as shown in FIGS. 1-3, the vaporization element itself can also be round or oval or the like in design.

The invention thus provides a compact and inexpensive vaporization element for liquids having a chemical heat source which has only a low space and weight requirement.

By the fact that the liquid to be vaporized reacts itself with the reagent, the additional water reservoir necessary in the aerosol vaporization device known from EP 0 371 282 A is superfluous. As a result, the weight, external dimensions and costs are considerably reduced. The vaporization element is therefore also suitable for a mobile inhalation apparatus and can easily be replaced after use, which renders possible convenient and hygienic handling.

The invention claimed is:

1. A vaporization element comprising:
   a first reservoir for storage of a liquid to be vaporized,
   a second reservoir, separated from the first reservoir by a first film, for storage of a reagent configured to carry out an exothermic chemical reaction upon contact with the liquid to be vaporized, wherein the liquid to be vaporized is an aqueous solution comprising caffeine or nicotine, or combinations thereof,
   a second film parallel to the first film for covering the first reservoir and positioned to contain the liquid within the first reservoir,
   a hinge configured to attach a cover part to a housing encasing the first reservoir and the second reservoir, the hinge configured to pivot the cover part with respect to the housing,
   an opening element configured with projections arranged on an underside of the cover part configured to perforate the first film to bring the reagent into contact with the liquid and configured to substantially simultaneously perforate the second film wherein perforations configured to open by the projections in the second film are configured for venting vaporized liquid, and wherein the cover part is provided with an opening for release of the vaporized liquid.

2. The vaporization element according to claim 1, further comprising a heat-resistant and waterproof housing comprising heat-resistant plastic or polycarbonate.

3. The vaporization element according to claim 1, wherein the first film comprises a layer of plastic.

4. The vaporization element according to claim 1, wherein the second reservoir contains an exothermically reactive substance mixture.

5. The vaporization element according to claim 4, wherein the exothermically reactive substance mixture contains calcium oxide.

6. The vaporization element according to claim 1, wherein the second film is made of a plastic material.

7. The vaporization element according to claim 1, comprising a wearable housing.

* * * * *